United States Patent [19]

Miller et al.

[11] 4,302,240

[45] Nov. 24, 1981

[54] ALKYL (MONO-, DI, TRI- AND TETRA-THIO)PHOSPHORYLATED ISOTHIAZOLIDIN-3-ONE 1-OXIDES AND 1,1-DIOXIDES

[75] Inventors: George A. Miller, Glenside; Ernest D. Weiler, Ambler, both of Pa.

[73] Assignee: Rohm and Haas Company, Philadelphia, Pa.

[21] Appl. No.: 99,268

[22] Filed: Dec. 3, 1979

Related U.S. Application Data

[62] Division of Ser. No. 635,477, Nov. 26, 1975, abandoned.

[51] Int. Cl.$^3$ .......................................... C07D 275/02
[52] U.S. Cl. ..................................... 71/090; 548/213; 424/270
[58] Field of Search ........................... 548/213; 71/90; 424/270

[56] References Cited

U.S. PATENT DOCUMENTS

| | | | |
|---|---|---|---|
| 3,523,121 | 8/1970 | Lewis et al. | 548/213 |
| 3,562,283 | 2/1971 | Lewis et al. | 548/213 |
| 3,957,808 | 5/1976 | Miller et al. | 548/213 |
| 4,062,859 | 12/1977 | Weiler et al. | 548/213 |
| 4,169,949 | 10/1979 | Weiler | 548/213 |

*Primary Examiner*—Nicholas S. Rizzo
*Attorney, Agent, or Firm*—Terence P. Strobaugh; George W. F. Simmons; William E. Lambert, III

[57] ABSTRACT

The preparation and use of alkyl (mono-, di-; tri- and tetra-thio)phosphorylated isothiazolidin-3-one 1-oxides and 1,1 dioxides are disclosed. These compounds and compositions containing them are useful pesticides and show activity in controlling insects, weeds and microorganisms such as bacteria, fungi, algae and the like.

10 Claims, No Drawings

ALKYL (MONO-, DI, TRI- AND TETRA-THIO)PHOSPHORYLATED ISOTHIAZOLIDIN-3-ONE 1-OXIDES AND 1,1-DIOXIDES

This is a division of application Ser. No. 635,477 filed Nov. 26, 1975 now abandoned.

SUMMARY OF THE INVENTION

This invention relates to certain novel substituted (mono-, di-, tri- and tetra-thio)phosphorylated isothiazolidin-3-one-1-oxides and 1,1-dioxides, to pesticidal compositions containing them and to their utilization in the control of pests such as insects, weeds and microorganisms such as bacteria, fungi, algae and the like.

The novel compounds of this invention are represented by the formula

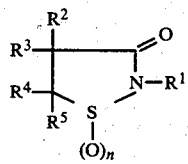

wherein $R^1$ is a hydrogen atom; an alkyl group, preferably having 1 to 18 carbon atoms; a cycloalkyl group, preferably having a 3 to 8 carbon atom ring and up to 12 carbon atoms; an aralkyl group having up to 11 carbon atoms; or an aryl group having up to 10 carbon atoms; $R^2$ and $R^5$ are independently a hydrogen atom, a halogen atom, preferably chloro or bromo, or an alkyl group preferably having 1 to 6 carbon atoms, more preferably 1 to 4 carbon atoms; at least one of $R^3$ and $R^4$ is independently a hydrogen atom or an alkyl group, preferably having 1 to 4 carbon atoms and the other is the group Z wherein Z is the group

wherein $R^6$ and $R^7$ are independently alkoxy or alkylthio groups of from 1 to 4 carbon atoms; X is oxygen or sulfur; and n is the integer 1 or 2.

The term "alkyl" as used in the specification and claims is meant to include branched and straight chain aliphatic hydrocarbons which can be unsubstituted or substituted with up to three substituents preferably one substituent, such as hydroxy groups, halogen atoms, carbalkoxy groups, cyano groups, carboxy groups and the like.

The term "aralkyl" as used in specification and claims is meant to include aralkyl groups of up to 11 carbon atoms preferably benzyl, which can be unsubstituted or substituted with up to three substituents preferably two substituents selected from the group consisting of halogen atoms, ($C_1$–$C_4$) alkyl groups, ($C_1$–$C_4$) alkoxy groups, nitro groups, cyano groups and the like.

The term "aryl" as used in the specification and claims is meant to include phenyl or naphthyl groups which can be unsubstituted or substituted with up to three substituents preferably up to two substituents selected from the group consisting of halogen atoms, ($C_1$–$C_4$) alkyl groups, ($C_1$–$C_4$) alkoxy groups, nitro groups, cyano groups and the like.

The preferred compounds of this invention are those wherein $R^1$ is an unsubstituted or hydroxy substituted alkyl group of from 1 to 18 carbon atoms; $R^2$ and $R^5$ are hydrogen or methyl; and one of $R^3$ or $R^4$ is the group

wherein $R^8$ is an alkyl group of from 1 to 4 carbon atoms; X is oxygen or sulfur; and n is the integer 1 or 2.

The most preferred compounds of this invention are those compounds wherein $R^1$ is an unsubstituted or hydroxy substituted alkyl group of from 1 to 8 carbon atoms; $R^2$ and $R^5$ are hydrogen and one of $R^3$ or $R^4$ is the group

and n is the integer 1 or 2.

Typical compounds which are encompassed by this invention include:

5-dimethylthiodithiophosphoryl-2-methyl-1-oxo-isothiazolidin-3-one 5-diethylthiodithiophosphoryl-1,1-dioxo-2-ethylisothiazolidin-3-one 5-dimethoxythiophosphoryl-2-isopropyl-1-oxoisothiozolidin-3-one 2-t-butyl-5-diethoxydithiophosphoryl-1,1-dioxoisothiazolidin-3-one 5-diisopropoxydithiophosphoryl-1-oxo-2-n-pentylisothiozolidin-3-one 5-di-n-butyldithiophosphoryl-1,1-dioxo-2-n-hexylisothiazolidin-3-one 5-diethylthiophosphoryl-2-methylheptyl-1-oxoisothiazolidin-3-one 5-diethylthiodithiophosphoryl-1,1-dioxo-2-n-octylisothiozolidin-3-one 5-dimethylthiodithiophosphoryl-2-sec-nonyl-1-oxoisothiazolidin-3-one 5-dimethoxydithiophosphoryl-2-n-decyl-1,1-dioxoisothiazolidin-3-one 5-diethoxydithiophosphoryl-2-sec-hendecyl-1-oxoisothiazolidin-3-one 5-dimethylthiothiophosphoryl-1,1-dioxo-2-n-dodecylisothiazolidin-3-one 5-di-n-propylthiodithiophosphoryl-2-n-hexadecyl-1-oxoisothiazolidin-3-one 5-dimethoxydithiophosphoryl-1,1-dioxo-2-n-octadecylisothiazolidin-3-one 5-ethoxy propylthiophosphoryl-2-hydroxymethyl-1-oxoisothiazolidin-3-one 5-ethoxypropylthiophosphoryl-2-hydroxypropyl-1,1-dioxoisothiazolidin-3-one 2-cyanoethyl-5-ethyoxypropylthiophosphoryl-1-oxoisothiazolidin-3-one 2-chloroethyl-4,5-dichoro-(4),5-diisopropoxythiophosphoryl-1,1-dioxo isothiazolin-3-one 2-cyanoheptyl-5-di-n-butylthiodithiophosphoryl-4,5-dichloro-1-oxo isothiazolidin-3-one 2-carbethoxymethyl-4,5-dimethyl-5-dimethylthiodithiophosphoryl-1,1-dioxo isothiazolidin-3-one 4-bromo-2-(2-carboxyethyl)-5-chloro-5-dipropylthiodithiophosphoryl-1-oxo isothiazolidin-3-one 2-cyclohexyl-5-hexyl-5-dimethoxythiophosphoryl-1,1-dioxo isothiazolidin-3-one 2-cyclooctyl-5-dimethoxythiophosphoryl-4-propyl-1-oxo isothiazolidin-3-one 2-benzyl-5-dimethoxydithiophosphoryl-1,1-dioxo-4-methyl isothiazolidin-3-one 5-dimethylthiothiophosphoryl-4-ethyl-1-oxo-2-phenethyl isothiazolidin-3-one 5-diethoxydithiophosphoryl-1,1-dioxo-2-(α-methylbenzyl)isothiazolidin-3-one 5-diethoxydithiophosphoryl-2-(β-methylphenethyl)-1-oxo-isothiazolidin-3-one 2-(2-chloro-4-methyl-6-methoxybenzyl)-5-diisopropylthiophosphoryl-1,1-dioxo-isothiazolidin-3-one 5-di-n-butoxydithiophosphoryl-2-(3,5-dimethoxyphenethyl)-1-oxo isothiazolidin-3-one 5-dimethoxythiophosphoryl-1,1-dioxo-2-(3-nitro-5-bromophenyl) isothiazolidin-3-one 4-cyanophenyl-4,5-dichloro-5-diethoxydithiophosphoryl-1-oxo isothiazolidin-3-one 2-(2-bromo-3-chloro-4-methylphenyl)-5-diethylthiodithiophosphoryl-1,1-dioxo isothiazolidin-3-one 5-diethoxydithiophosphoryl-1-oxo-2-(2,4,6-trichlorophenyl) isothiazolidin-3-one 5-diethoxydithiophosphoryl-1,1-dioxo-2-(1-naphthylmethyl) isothiazolidin-3-one 2-[2-(4-ethoxynaphthyl)]-5-ethoxypropylthiothiophosphoryl-1-oxo isothiazolidin-3-one The alkyl(mono-, di-, tri- and tetra-thio)phosphorylated isothiazolidin-3-one 1-oxides and 1,1-dioxides of this invention can be prepared by a variety of synthetic routes. One method involves the following reaction scheme:

Scheme A

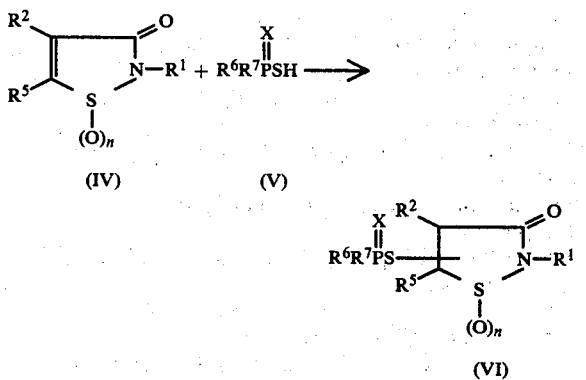

Methods for the preparation of the 1-oxo-and 1,1-dioxo-3-isothiazolones of Formula (IV) are described in U.S. Pat. No. 3,562,283 granted Feb. 9, 1971 to Sheldon N. Lewis and George A. Miller, assigned to a common assignee which is herein incorporated by reference. The phosphates of Formula (V) are commercially available materials or they are prepared by procedures well known in the art e.g. in "Methoden der Organischen Chemie" (Hauben-Weyl) vol. 12, part 2, page 598–748 (1964).

In this invention it has not been ascertained as to whether the thiophosphate has added to the isothiazolone in the 4 or 5 position however, it is believed that the thiophosphate addition occurs in the 5 position.

The alkyl(mono-, di-, tri- and tetra-thio)phosphorylated isothiazolidin-3-one 1,1-dioxides of this invention can also be prepared by reaction Scheme B:

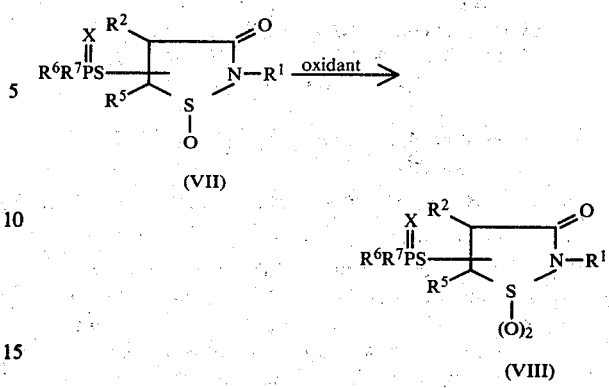

The methods for the preparation of the compounds of Formula (IV) are described in U.S. Pat. No. 3,523,121 granted Aug. 4, 1970 to Sheldon N. Lewis et al. assigned to a common assignee which is incorporated herein by reference. In the general method of preparation for the compounds of this invention the substituted 4-isothiazolin-3-one 1-oxides or 1,1-dioxides are first dissolved in an appropriate solvent such as benzene, toluene, acetonitrile, ethyl acetate, dimethylformamide, acetone, methanol, propanol and the like or mixtures thereof. To this solution is then added at least an equimolar amount of a dialkyl substituted mono-, di-, tri- or tetra-thiophosphate at temperatures from about 5° C. to about 100° C. for periods anywhere from about one hour to about one week depending upon the rate of reaction, temperature and solvent employed. In order to facilitate the reaction a base such as sodium methoxide, sodium ethoxide, potassium t-butoxide, sodium hydride and the like can be added to the reaction either neat or as a solution dissolved in a minimum amount of an appropriate solvent. The solvent is then removed and the resultant residue is isolated by normal extraction and recrystallization procedures.

The 1-oxide derivative Formula (VII) can be directly oxidized to the 1,1-dioxide derivatives by employing various types of oxidizing agents including peracids such as hydrogen peroxide, performic acid, peracetic acid, perphthalic acid, perbenzoic acid, m-chloroperbenzoic acid, nitric acid, and chromic compounds such as chromium trioxide and chromic acid-sulfuric acid (Jones' reagent).

To prepare the 1,1-dioxide derivative at least two equivalents are theoretically required, but three or more equivalents can be used. Although the oxidations can be run in the absence of a solvent, the use of a solvent is preferred. Any solvent which is not itself oxidized can be used and solvents in the ester, ketone, aliphatic and aromatic hydrocarbon and chlorinated hydrocarbon classes are commonly employed. The chlorinated aliphatic hydrocarbons are preferred. The reactions can be run at temperatures from about −5° C. to about 60° C. with the lower temperatures, e.g., from about 15° C. to about 40° C. being preferred for the 1-oxide derivatives and the higher temperatures, e.g., from about 25° C. to about 50° C. being preferred for the 1,1-dioxide derivatives.

When chromic acid is used as the oxidizing agent, it can be employed in from about 1.0 to about 2 or more equivalents. An inert solvent, such as a ketonic solvent, is commonly employed although the oxidation will proceed in the absence of a solvent. The reaction is usually run at about room temperature, but will proceed at temperatures from about 0° to about 60° C. with from about 15° C. to about 35° C. being preferred.

The following examples are provided to enable one skilled in the art to better understand this invention, and are not to be considered as limitations of the scope thereof.

EXAMPLE I

4 or 5 Diethyldithiophosphoryl-2-n-octyl-isothiazolidin-3-one 1,1-dioxide

To a solution of 2.45 g (0.01 mole) of 2-n-octyl-4-isothiazolin-3-one 1,1-dioxide in 50 ml. of benzene is added 2.0 g (0.011 mole) of diethyldithiophosphate and 2–3 drops of a saturated sodium methoixde/methanol solution. The solution is heated at reflux for 24 hours, cooled and washed three times with 25 ml. of a 10% KOH solution. The benzene solution is then washed with water, diluted with ether and dried over magnesium sulfate. The solution is concentrated to give 2.3 g (53%) of product as a thick oil.

EXAMPLE II

4 or 5 Diethyldithiophosphoryl-2-n-octyl-isothiazolidin-3-one 1-oxide

To a solution of 2.3 g (0.01 mole) of 2-n-octyl-4-isothiazolin-3-one 1-oxide in 50 ml of benzene is added 2.0 g (0.011 mole) of diethyldithiophosphate. The solution is heated at reflux for 5½ hours, cooled and washed three times with a 10% KOH solution. The solution is then washed with water until neutral to litmus. The benzene solution is diluted with ether, dried over magnesium sulfate and concentrated to provide 3.3 g (79%) of product as a thick yellow oil.

EXAMPLE III

4 or 5 Diethyldithiophosphoryl-2-ethyl-isothiazolidin-3-one 1-oxide

To a solution of 7.25 g (0.25 mole) of 2-ethyl-4-isothiazolin-3-one 1-oxide in 100 ml of benzene is aded 10.23 g (0.055 mole) of diethyldithiophosphate. The mixture is evaporated under reduced pressure and the residue is dissolved in ether. The ether solution is washed with 5% sodium hydroxide solution and dried over sodium sulfate. Evaporation of the dry solution gives an oil which partially solidifies. Crystallization from ethanol gives 4.7 g (28%) of a white solid, m.p. 71°-74° C.

EXAMPLE IV

4 or 5 Diethyldithiophosphoryl-2-ethyl-isothiazolidin-3-one 1,1-dioxide

To a solution of 1.61 g (0.01 mole) of 2-ethyl-4-isothiazolin-3-one, 1,1-dioxide in 20 ml. of benzene is added 2.05 g (0.011 mole) of diethyldithiophosphate. The clear solution is heated at reflux for 4 hours and allowed to cool and stand at room temperature for about 65 hours. The solution is evaporated to give a pale yellow oil. The oil is taken up in 200 ml. of ether. The ether solution is washed with a solution of 0.5 g of sodium hydroxide in 50 ml. of water and then with 20 ml. of water. The other solution is dried over anhydrous magnesium sulfate, filtered and concentrated to provide 2.54 g (73%) of crude product as a thick, pale orange oil. The latter is purified by dry column chromatography (silica gel and benzene) to provide purified product.

EXAMPLE V

4 or 5 Diethyldithiophosphoryl-2-methyl-isothiazolidin-3-one 1-oxide

To a solution of 3.95 g (0.03 mole) of 2-methyl-4-isothiazolin-3-one 1-oxide in 50 ml. of benzene is added 5.6 g (0.03 mole) of diethyldithiophosphate and 3 drops of saturated sodium methoxide/methanol solution. The clear solution is stirred and maintained at 50° C. for 20 hours. The solution is cooled and concentrated to yield a thick oil. The oil is taken into 80 ml. of ether, washed with 5 ml. of 3 N sodium hydroxide solution and water. The ether solution is dried over magnesium sulfate and concentrated to yield 4.8 g (51%) of product, m.p. 71°-74° C.

EXAMPLE VI

4 or 5 Diethylthiophosphoryl-2-methyl-isothiazlidin-3-one 1-oxide

To a solution of 1.31 g (0.01 mole) of 2-methyl-4-isothiazolin-3-one 1-oxide in 15 ml. of benzene is added 1.8 g. (0.01 mole) of diethylthiophosphate and 3 drops of saturated sodium methoxide/methanol solution. The clear solution is stirred at room temperature for one week. The solution is concentrated and yields a thick oil. The oil is taken into 150 ml. ethyl acetate, washed twice with 10 ml. of 1 N sodium hydroxide solution and twice with 10 ml. of water. The ether solution is dried over magnesium sulfate, concentrated and triturated with ether to afford 0.35 g (12%) of product, m.p. 72°-75° C.

EXAMPLE VII

4 or 5 Diethyldithiophosphoryl-2-hydroxymethyl-isothiazolidin-3-one 1-oxide

A 5.7 g (0.05 mole) sample of 4-isothiazolin-3-one 1-oxide is dissolved in 6 ml. (0.06 mole) of aqueous formaldehyde solution (38%). To this clear solution is added 9.8 g (0.05 mole) of diethyldithiophosphate. The reaction which exotherms slightly, is cooled and stirred at room temperature for about 65 hours. The mixture is then taken into 200 ml. of ethyl acetate washed with 3 N sodium hydroxide solution and then water. The ethyl acetate solution is dried over magnesium sulfate and concentrated to give 14.0 g (84%) of product as a thick yellow oil.

The following Table I presents the elemental analysis and melting points of the compounds prepared via the above experimental procedures.

TABLE I

| Example No. | mp° C. | Elemental Analyses Found/(calc'd) | | | | |
|---|---|---|---|---|---|---|
| | | C | H | N | S(O) | P |
| 1 | oil | 43.51 | 8.02 | 3.14 | 21.66 | 6.72 |
| | | (41.75) | (7.01) | (3.24) | (22.29) | (7.18) |
| 2 | oil | 42.29 | 7.89 | 2.84 | 23.77 | 8.71 |
| | | (43.35) | (7.28) | (3.37) | (23.15) | (7.45) |
| 3 | 71–74 | 32.99 | 5.66 | 4.20 | 29.08 | 9.25 |
| | | (32.63) | (5.44) | (4.23) | (29.00) | (9.36) |
| 4 | oil | 31.74 | 5.80 | 3.81 | 29.03 | 9.44 |
| | | (31.13) | (5.19) | (4.03) | (27.66) | (8.93) |

TABLE I-continued

| Example No. | mp° C. | Elemental Analyses Found/(calc'd) | | | | |
| --- | --- | --- | --- | --- | --- | --- |
| | | C | H | N | S(O) | P |
| 5 | 71–74 | 30.70 | 5.22 | 4.45 | 30.08 | 9.86 |
| | | (30.28) | (5.08) | (4.41) | (30.31) | (9.76) |
| 6 | 72–75 | 32.08 | 5.62 | 4.67 | 21.29 | 10.03 |
| | | (31.89) | (5.35) | (4.64) | (21.28) | (10.28) |
| 7 | oil | 29.63 | 4.99 | 3.83 | 28.43 | 9.50 |
| | | (28.82) | (4.82) | (4.20) | (28.84) | (9.29) |

The alkyl mono-, di-, tri-, and tetra-thiophosphorylated isothiazolidin-3-one 1-oxides and 1,1-dioxides of this invention are used for the protection of plants and animals, including man, from the ravages of harmful and annoying pests or disease organisms which they may carry. The term "pest" as used herein is intended not only to include arthropods, such as insects and acarids in all stages of development as well as nematodes in all stages of development but also weeds and microorganisms such as bacteria, fungi, algae and the like.

Fungi for which the compounds of this invention have shown control include powdery mildew (*Erysiphe polygoni*), rice blast (*Piricularia oryzae*), tomato late blight (*Phytophthora infestans*), grade downy mildew (*Plasmopora viticola*), *Aspergillus niger* and *Rhizopus stoloninfer*. Bacteria for which the compounds of this invention have shown control include *Pseudomonas aeruginosa Streptococus aureus* and *Escherichia coli*.

These compounds have also exhibited postemergence herbicidal activity against both monocotyledons and dicotyledons.

Certain compounds of this invention are particularly useful arthropodicides and are notable for their rapidity of action as evidenced by house fly knockdown. Other compounds effectively control nematodes such as the southern root knot nematode (*Meloidogyne incognita*).

The arthropods which are controlled by compounds of this invention include the two-spotted spider mite (*Tetranychus urticae*) the green peach aphid (*Myzus persicae*) the Mexican bean beetle (*Ephilachna varivestis*), the southern armyworm (*Spodoptera eridania*), the house fly, (*Musca domestica*) the German cockroach (*Blattella germanica*), the southern corn rootworm (*Diabrotica undecimpunctata howardi*) and the yellow fever mosquito larvae (*Aedes aegypti*).

The novel alkyl(mono-, di-, tri-, and tetrathio)phosphorylated isothiazolidin-3-one 1-oxides and 1,1-dioxides of this invention are active pesticides. Representative compounds demonstrate control of various pests such as mites, insects, weeds and microoragnisms such as bacteria, fungi and algae.

Generally, control of a living organism is achieved in accordance with this invention by application of the compounds in pesticidally effective amounts either directly to the pests to be controlled or to the loci to be freed of or protected from attack by such pests. For example, food, fiber, forage, forest, and ornamental crops and stored products thereof would represent plant protection loci. Treatment, with compounds of this invention of domestic animals, man and their immediate environs similarly constitute representative loci for protection against various annoying ectoparasitic or endoparasitic Acarina (Acari) and Insecta. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence of growth of a living organism. Such means can comprise a complete killing action, eradication, arresting in growth, inhibition, reduction in number or any combination thereof.

The compounds of this invention can be readily utilized as slimicides, algaecides, bactericides, and fungicides in any locus and particularly in aqueous media, such as, for example, paper pulp processes, aqueous polymer dispersions, water-based paints, and the like. In addition, these compounds and compositions containing them can function as, for example, fabric and leather preservatives, soap additives, sanitizing agents, such as in laundry soaps and detergents, preservatives for metal working compounds such as emulsifiable cutting oils, preservatives for fuels, fiber spin finish biocides and the like.

The isothiazolidinone 1-oxide and 1,1-dioxides of the invention are also useful as laundry sanitizing agents, in which fast speed-of-kill is particularly advantageous. Generally, about 0.01 to about 10% by weight and preferably about 0.05 to about 5% by weight, of the isothiazolidinone oxide will be added to a soap detergent to make a sanitizing laundry composition. Isothiazolidinone oxides can also be added directly to the laundry wash water, generally at a concentration of about 0.5 to about 1000 parts per million by weight.

The isothiazolidinone 1-oxides and 1,1-dioxides of the invention are also useful as paint preservatives and paint fungistats. Microbial activity in water-based and oil-based paint emulsions is inhibited when the isothiazolidinone oxides paint emulsions is inhibited when the isothiazolidinone oxides are incorporated into the paint. The isothiazolidinone oxides are also mildewcides for paint films when incorporated in paint formulations.

The isothiazolidinone 1-oxide an 1,1-dioxides of this invention are useful as agricultural bactericides and fungicides. As such as they are particularly valuable when formulated in bactericidal and fungicidal compositions. Such compositions normally comprise an agronomically acceptable carrier and an isothiazolidinone 1-oxide or 1,1-dioxide or mixture of isothiazolidinone oxides as the active agent. Where necessary or desirable, surfactants or other additives may be incorporated to give uniformally formulated mixtures. By "agronomically acceptable carrier" is meant any substance which can be utilized to dissolve, disperse, or diffuse the chemical incorporated therein without impairing the effectiveness of the toxic agent and which does no permanent damage to the environment, soil, equipment, or agronomic crops.

In general, a locus subject to contamination by microorganisms can be protected in accordance with this invention by incorporating into the locus an isothiazolidinone 1-oxide or 1,1-dioxide in an amount which is effective to control the microorganisms. The term "contamination" is meant to include attack by microorganisms which lead to a chemical or physical breakdown or disintegration of the locus as well as proliferation of the microorganisms within the locus without an accompanying deleterious effect. The exact amount of isothiazolidinone 1-oxide or 1,1-dioxide required will of course, vary with the medium being protected, the microogranisms being controlled, the particular isothiazolidinone oxides or compositions containing the isothiazolidinone oxides being employed, the degree of control desired, and other factors. Typically, in a liquid medium suitable control is obtained when the isothiazolidinone oxides are incorporated in the range of from about 0.1 to about 10,000 parts per million (ppm) of from about 0.00001 to about 1% based on the weight of the medium. A range of about 1 to 2000 ppm is preferred.

For use as pesticides the compounds of this invention can be used as solutions in organic solvents or formulations. For example, they can be formulated as wettable powders, emulsifiable concentrates, dusts, granular formulations of flowable emulsifiable concentrates. In such formulations, the isothiazolidinone oxides are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual."

The isothiazolidinone oxides can be taken up or mixed with a finely particled solid carrier, as for example, clays, inorganic silicates, carbonates, and silicas. Organic carriers can also be employed. Dust concentrates are commonly made wherein compounds are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The compounds are usually present in the range of about 10 to about 80% by weight and surfactants from about 0.5 to about 10% by weight.

One convenient method for preparing a solid formulation is to impregnate the compounds onto the solid carrier by means of a volatile solvent such as acetone. In this manner adjuvants, such as activators, adhesives, plant nutrients, synergists and various surfactants can also be incorporated.

Emulsifiable concentrate formulations can be prepared by dissolving the alkyl (mono-, di-, tri- and tetra-thio)phos phorylated isothiazolidin-3-one 1-oxides and 1,1dioxides of this invention in an agronomically acceptable organic solventsoluble emulsifying agent. Suitable solvents are usually waterimmiscible and can be found in the hydrocarbon, ketone, ester, alcohol and amide groups of organic solvents. Mixtures of solvents are commonly employed. The surfactants useful as emulsifying agents can constitute about 0.5 to about 10% by weight of emulsifiable concentrate and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. Usually, this will involve the application of the alkyl(amino-, di-, tri-, and tetra-thio)phosphorylated-isothiazolidin-3-one 1-oxides and 1,1-dioxides to the loci to be protected from or freed of pests in an effective amount when incorporated in an agronomically acceptable carrier. However, in certain situations it may be desirable and advantageous to apply the compounds directly onto the loci to be protected from or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents. The application rate will, of course, vary depending upon the purposes for such application, the compound being utilized, the frequency of dissemination and the like.

For use as insecticides and acaricides, dilute sprays can be applied at concentrations of about 0.001 to about 20 pounds of active ingredient per 100 gallons of spray. They are usually applied at about 0.01 to about 5 pounds per 100 gallons. In more concentrated sprays, the active ingredient is increased by a factor of about 2 to about 12. With dilute sprays, applications are usually made to the plants until run off is achieved whereas with more concentrated low-volume sprays, the materials are applied as mists.

For use as a nematocide or as soil insecticide, the compounds can be applied as a solid formulation, preferably a granular formulation, by broadcasting, side dressing, soil incorporation or seed treatment.

The compositions can also be added to transplant water or employed as dips or soaks for vegetative parts employed in propagation, such as seeds, tubers, roots, seedlings, etc., so as to disinfect and/or provide residual protection from nematodes. The application rate can be from about 1 to about 50 pounds per acre; however, higher rates can also be used. The preferred rate is from about 1 to about 25 pounds per acre. For soil incorporation, the compounds of this invention can be mixed with the soil at a rate of about 2 to about 100 ppm. of active ingredient.

The compounds of this invention can be utilized as the sole pesticidal agents or they can be employed in conjunction with other bactericides, fungicides, herbicides, insecticides, acaricides, nematocides and comparable pesticides.

Many variations of this invention are possible without departing from the spirit or scope thereof.

We claim:

1. A compound of the formula

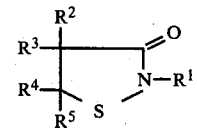

wherein
$R^1$ is hydrogen; $(C_1-C_{18})$ alkyl or $(C_1-C_{18})$ alkyl substituted with up to three substituents selected from the group consisting of hydroxy, halogen, carbalkoxy, cyano and carboxy; $(C_3-C_8)$ cycloalkyl; phenylalkyl having up to 11 carbon atoms or phenylalkyl having up to 11 carbon atoms substituted with up to three substituents selected from the group consisting of halogen, $(C_1-C_4)$ alkyl, $(C_1-C_4)$ alkoxy, nitro and cyano; phenyl or naphthyl or phenyl or naphthyl substituted with up to three substituents selected from the group consisting of halogen, $(C_1-C_4)$ alkyl, $(C_1-C_4)$ alkyl, $(C_1-C_4)$ alkoxy, nitro and cyano;

$R^2$ and $R^5$ are independently hydrogen, halogen or $(C_1-C_6)$ alkyl;

one of $R^3$ and $R^4$ is independently hydrogen or $(C_1-C_4)$ alkyl and the other is the group Z wherein Z is

wherein $R^6$ and $R^7$ are independently $(C_1-C_4)$ alkoxy or $(C_1-C_4)$ alkylthio;

X is oxygen or sulfur; and n is the integer 1 or 2.

2. A compound according to claim 1 wherein X is sulfur and $R^1$ is $(C_1-C_8)$ alkyl.

3. A compound according to claim 2 wherein $R^3$ is the group diethoxydithiophosphoryl.

4. A compound according to claim 3 wherein $R^4$ is the group diethoxydithiophosphoryl.

5. A compound according to claim 4 wherein $R^1$ is n-octyl and n is the integer 1.

6. A compound according to claim 4 wherein n is the integer 2.

7. A compound according to claim 6 wherein $R^1$ is n-octyl.

8. A method for controlling pests which comprises applying to the pest or to the locus to be protected from or freed of the pest an effective amount of a compound of claim 1.

9. A pesticidal composition for controlling pests which comprises an inert carrier and as the active ingredient a compound of claim 1.

10. A method for controlling pests which comprises applying to the pests or to the locus to be protected from or freed of the pests an effective amount of a composition according to claim 9.